United States Patent [19]

Nakajima et al.

[11] 4,130,571

[45] Dec. 19, 1978

[54] PROCESS FOR PREPARING 1,2-DIACYL-3-GLYCERYLPHOSPHORYL-CHOLINES

[75] Inventors: Tadashi Nakajima, Takatsuki; Yasuji Soda, Kobe; Kenichi Kashima, Fujiidera; Haruyoshi Kudoh, Ibaraki; Akira Miyamoto, Nishinomiya, all of Japan

[73] Assignee: Nippon Shoji Kaisha, Ltd., Osaka, Japan

[21] Appl. No.: 652,319

[22] Filed: Jan. 26, 1976

[30] Foreign Application Priority Data

Feb. 4, 1975 [JP] Japan ............................ 50-15143

[51] Int. Cl.² .................................................. A23J 7/00
[52] U.S. Cl. ............................. 260/403; 252/301.1 R; 252/431N; 252/438; 252/476
[58] Field of Search .................. 260/403; 252/431 N, 252/438, 476

[56] References Cited

U.S. PATENT DOCUMENTS

| 3,270,084 | 8/1966 | Schriesheim et al. | 260/632 B |
|---|---|---|---|
| 3,592,829 | 7/1971 | Betzing | 260/403 |

OTHER PUBLICATIONS

Slotboom, A. J. et al., "Hydrolysis of Phosphoglycerides by Purified Lipase Preparations. Preparation of Unsaturated 2-monoacylocholine Phosphoglycerides" Chem. Phys. Lipids, vol. 4, pp. 30-36 (1970).

Boss, W. F. et al., "Novel Synthesis of Spin Label Derivatives of Phosphatidylcholine" Anal. Biochem 64 (1) 1975, pp. 289-292.

Foerst, W. - Newer Methods of Preparative Organic Chemistry - vol. V, 1968, Academic Press NYC., "Syntheses Using Heterocyclic Amides (Azolides), pp. 61-63, pp. 74-77, 91.

Pugh, E. L. et al., "Simplified Procedure for Synthesis of Diacyl Carbon-labeled Lecithins"- J. Lipid Res. 16 (5) 1975, pp. 392-394.

*Primary Examiner*—Helen M. McCarthy
*Attorney, Agent, or Firm*—Stevens, Davis, Miller & Mosher

[57] ABSTRACT

Improved process for preparing 1,2-diacyl-3-glycerylphosphorylcholines, wherein the diacyl groups are, different or the same, a residue of a saturated or unsaturated fatty acid, particularly one of the acyl groups being a residue of a highly unsaturated fatty acid or being a residue of a saturated or unsaturated fatty acid labelled with an isotope, which comprises acylating a glyceryl-phosphorylcholine or monoacyl derivative thereof or the salt thereof with an acylating agent (e.g. 1-acylimidazole or 4-acyl-3-phenyl-1,2,4-oxadiazol-5-one) in the presence of a catalyst (e.g. an alkali salt of a nitrogen-containing 5-membered heterocyclic compound or sodium oxide).

23 Claims, No Drawings

PROCESS FOR PREPARING 1,2-DIACYL-3-GLYCERYLPHOSPHORYLCHOLINES

The present invention relates to an improved process for preparing 1,2-diacyl-3-glycerylphosphorylcholines. More particularly, it relates to a process for preparing 1,2-diacyl-3-glycerylphosphorylcholines of the formula:

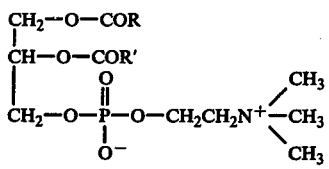

wherein R and R' are different or the same and are each a residue of a saturated or unsaturated fatty acid.

The compound of the formula (I) is so-called lecithin, which is one of glycerylphospholipids and occupies 50 or more % of the phospholipids contained in various animals and plants. The natural lecithin contains mainly a residue of a saturated fatty acid (e.g. myristic acid, palmitic acid, or stearic acid) and/or a residue of an unsaturated fatty acid (e.g. oleic acid, linoleic acid, or linolenic acid) as the acyl group (RCO-13). Among these, the lecithin containing a large amount of a highly unsaturated fatty acid, such as linoleic acid or linolenic acid, which is an essential fatty acid, has been recently used as a medicament because of its excellent biological activities. Moreover, since around 1960, when it has been found that the lecithin is one of the basic components of various biomembranes, the importance of the lecithin has progressively increased in the medical and pharmaceutical fields.

However, it is very difficult to prepare a lecithin having a specific fatty acid residue or a fatty acid residue labelled with an isotope, particularly having the different kinds of fatty acid residue at the 1- and 2-positions (so-called, "mixed acids type" lecithin).

There have, hitherto, been reported various processes for preparing diacylglycerylphosphorylcholines. For instance, Baer et al have reported that the compound can be prepared by introducing the phosphate moiety into a diglyceride or a diacylglyceryl-iodohydrin and subsequently combining thereto the choline moiety, as shown in the following reaction scheme (E. Baer & M. Kates; J. Am. Chem. Soc., Vol. 72, page 942, 1950):

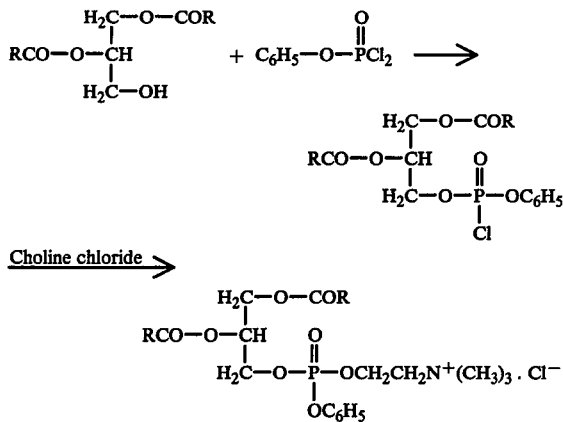

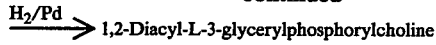

However, according to this process, the desired compound is obtained in a very low yield, and it is not economical.

There are also known processes for introducing a specific fatty acid residue into a glyceryl-phosphorylcholine (hereinafter, referred to as "GPC") by an acid chloride method or an acid anhydride method. For instance, Baer et al have reported that dimyristoyl derivative (yield: 51.0%), distearoyl derivative (yield: 38.4%) and dioleoyl derivative (yield: 54.7%) could be obtained by an acid chloride method, i.e. by reacting cadmium chloride salt of GPC with a fatty acid chloride at room temperature for 3 hours (E. Baer et al.; Can. J. Biochem. Physiol., Vol. 37, page 953, 1959). The present inventors have tried to increase the yield of the product in this process by prolonging the reaction time, but it resulted in the increase of the by-products (Baer et al said that the by-products might be cyclic compounds). There is no report on the preparation of a highly unsaturated fatty acid derivative by this process.

Besides, Cubero Robles et al have proposed an acid anhydride method in order to prevent the production of the by-product in the acid chloride method (E. Cubero Robles et al.; Biochem. Biophys. Acta, Vol. 187, page 520, 1969). According to this process, there were obtained dipalmitoyl derivative (yield: 90%), distearoyl derivative (yield: 81%) and dioleoyl derivative (yield: 70%) by reacting cadmium chloride salt of GPC with a fatty acid anhydride and tetraethyl ammonium salt of a fatty acid. This process can give the desired diacyl derivatives in a comparatively high yield in case of stable saturated fatty acid derivatives, but it is not necessarily suitable for the preparation of unsaturated fatty acid derivatives. Only one example of oleic acid derivative, which has an unsaturation degree of 1, has been reported, and it has been considered that this process can not be applied to highly unsaturated fatty acids derivative, such as linoleic acid. Recently, Gordon has reported that dioleoyl derivative could be obtained by an acid anhydride method (G. T. Gordon; Lipid, Vol. 7, page 261, 1972), in which the desired compound (yield: 67%) was obtained by reacting a mixture of GPC, linolic anhydride and potassium linolate (1:2:2 by weight) at 44° C. for 60 hours. However, in this process, the linoleic anhydride and the alkali metal salt of linoleic acid must be prepared separately and it is very difficult to prepare the starting materials labelled with isotope which should be prepared in trace amounts, and further the starting fatty acid is required twice of the theoretical amount. Thus, this process is not economical, either.

Moreover, it has, very recently, been reported that labelled lecithins could be prepared by reacting directly a lysolecithin with an acylimidazole intermediate (W. F. Boss et al.; Analytical Biochemistry, Vol. 64, pages 289–292, 1975). However, even by this process, the desired diacyl derivatives can not be obtained in a high yield, and further, it is impossible to obtain a derivative of highly unsaturated fatty acids.

Under the circumstances, the present inventors have intensively studied to find an improved process for preparing 1,2-diacyl-3-glycerylphosphorylcholines having particularly a highly unsaturated fatty acid residue, and more particularly, having different kinds of fatty acid residue at the 1- and 2-positions, and have found that the desired compounds can be prepared in a high yield and in a high purity by acylating glycerylphosphorylcholine (GPC) or monoacyl derivative thereof or the salt thereof with a specific acylating agent in the presence of a specific catalyst.

An object of the present invention is to provide an improved process for preparing 1,2-diacyl-3-glycerylphosphoryl-cholines.

Another object of the invention is to provide a process for preparing highly unsaturated fatty acid derivatives of lecithin.

A further object of the invention is to provide a process for preparing mixed acids type lecithins.

A still further object of the invention is to provide a process for preparing labelled lecithins.

These and other objects of the invention will be apparent from the description hereinafter.

According to the present invention, the desired 1,2-diacyl-3-glycerylphosphorylcholines are prepared by acylating a GPC or monoacyl derivative thereof or the salt thereof with an acylating agent selected from the group consisting of 1-acylimidazole and 4-acyl-3-phenyl-1,2,4-oxadiazol-5-one in the presence of a catalyst selected from the group consisting of an alkali salt of a nitrogen-containing 5-membered heterocyclic compound and sodium oxide.

The starting GPC may be used in the form of the free base or its salt, for example, cadmium chloride salt or barium chloride salt. These salts are usually considered to be a complex compound. The GPC and a process for the preparation thereof are described, for instance, in H. Brockerhoff et al.; Can. J. Biolchem., Vol. 43, page 1777 (1965) and J. S. Chadha; Chem. Phys. Lipids., Vol. 4, page 104 (1970).

The monoacyl derivatives of GPC, i.e. monoacyl-3-glycerylphosphorylcholines, which are alternatively named as 1(or 2)-acyl type lysolecithins, include 1-monoacyl derivatives and 2-monoacyl derivatives, which may be also used in the form of the free base or its salt with cadmium chloride or barium chloride. The 1-monoacyl-3-glycerylphosphorylcholines are usually prepared by hydrolyzing a natural or synthetic lecithin with phospholipase $A_2$ or an analogous enzyme thereof, as shown in the following scheme:

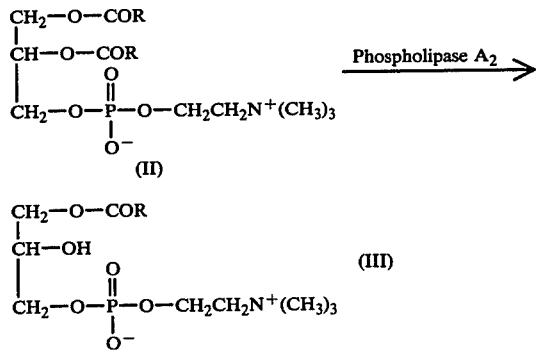

wherein R is a residue of a saturated or unsaturated fatty acid.

The enzyme: phospholipase $A_2$ or the analogous enzyme is usually obtained from snake venoms (e.g. Crotalus admanteus venom, Naja naja venom, or Trimeresurus flavoviridis venom), bee venoms (e.g. Apis mellifera venom), gila monster venoms (e.g. Heloderma horidum venom), scorpin venoms (e.g. Leurus quinques triatus venom), or various organs of animals (e.g. pig pancreas, or rat liver). The hydrolysis should be carried out carefully for preventing undesired rearrangement of the acyl group, and is usually carried out by treating the lecithin with the enzyme in an appropriate solvent (e.g. ethyl ether) in the presence of a buffer solution (pH: 7.0–7.2, e.g. 0.2 M boric acid-sodium carbonate buffer solution, 0.2 M Tris buffer solution) and an activating agent (e.g. calcium chloride) at room temperature.

The 2-monoacyl-3-glycerylphosphorylcholines are, likewise, prepared by hydrolyzing a natural or synthetic lecithin with phospholipase $A_1$ or an analogous enzyme thereof, which is obtained from various bacteria (e.g. *Escherichia coli, Mycobacterium phlei, Bacillus megaterium,* or *Bacillus subtilis*) or various organs of animals (e.g. bovine pancreas, or rat thymus, kidney, pancreas or lung).

Besides, the purity of the monoacyl derivatives, as the 1-monoacyl derivative or the 2-monoacyl derivative, can be determined by enzymatically hydrolyzing the monoacyl-3-glycerylphosphorylcholine with phospholipase C, whereby the phosphorylcholine moiety is split off to give a monoglyceride, and then analyzing the resulting monoglyceride.

The acylating agent: 1-acylimidazoles can be easily prepared by reacting N,N'-carbonyldiimidazole with a fatty acid by a conventional method. Alternatively, the 1-acylimidazoles can be prepared by reacting imidazole with a fatty acid chloride [H. A. Staab; Chem. Ber., Vol. 89, page 1940 (1956)]. The 4-acyl-3-phenyl-1,2,4-oxadiazol-5-ones can be also easily prepared by reacting 3-phenyl-1,2,4-oxadiazol-5-one with a fatty acid by a conventional method. These acylating agents may be used after isolating from the reaction mixture, or in the form of the reaction mixture as it is. Besides, the acylating agent may be used in an amount of an equimolar or slightly excess amount (usually about 1–3 times of stoichiometric amount) on the basis of the starting GPC or monoacyl derivative thereof.

The fatty acids include saturated fatty acids having 10 to 22 carbon atoms (e.g. capric acid, lauric acid, myristic acid, palmitic acid, stearic acid, arachidic acid, behenic acid, etc.) and unsaturated fatty acids having 14 to 20 carbon atoms (e.g. myristoleic acid, palmitoleic acid, oleic acid, linoleic acid, linolenic acid, arachidonic acid, etc.). Preferred fatty acids are highly unsaturated fatty acids having two or more double bonds, such as linoleic acid, linolenic acid and arachidonic acid. These fatty acids may be labelled with an isotope (e.g. $^{14}C$ or $^3H$).

The catalyst may be an alkali salt of nitrogen-containing 5-membered heterocyclic compound, such as imidazole sodium salt, triazole sodium salt, benzimidazole sodium salt, or other alkali metal salt (e.g. potassium salt) of these heterocyclic compounds. Sodium oxide may also be used as the catalyst.

The compounds of the present invention include an asymmetric carbon atom in the molecule, and therefore, may be present as D- or L-optical isomer or racemic substance. Unless otherwise specified in the description and accompanying claims, it is intended to include all isomers, whether separated or mixtures thereof.

The process of the present invention will be illustrated, in case of using 1-acylimidazole as the acylating agent, by the following reaction scheme:

$$\begin{array}{l} CH_2-O-R'' \\ CH-O-R''' \\ CH_2-O-\underset{\underset{O^-}{|}}{\overset{\overset{O}{\|}}{P}}-O-CH_2CH_2N^+(CH_3)_3 \end{array} \quad (I)$$

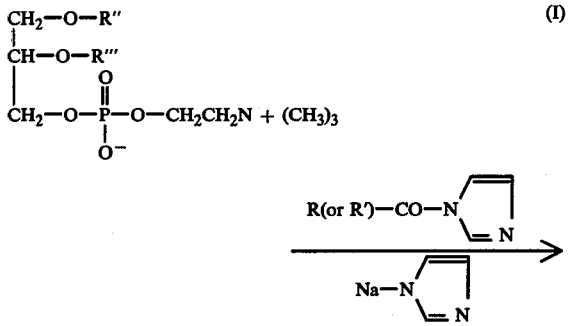

wherein R and R' are as defined above, and R'' is hydrogen or the same as R and R''' is hydrogen or the same as R', provided that both of R'' and R''' are concurrently not a group other than hydrogen.

The process of the present invention is described in more detail below, in case of using 1-acylimidazole as the acylating agent.

N,N'-Carbonyldiimidazole is suspended in anhydrous tetrahydrofuran (hereinafter, referred to as "THF"), and to the suspension is added a saturated or unsaturated fatty acid. The mixture is agitated ten several to several tens of hours in an inert gas (e.g. nitrogen gas) to give 1-acylimidazole. This compound is used for the acylation after isolated or in the form of the reaction mixture as it is.

To a mixture of GPC (both of R'' and R''' in the formula (IV) are hydrogen) or monoacyl derivative thereof (one of R'' and R''' in the formula (IV) is hydrogen and the another one is a group other than hydrogen) or the salt thereof and 1-acylimidazole obtained above in anhydrous THF is added imidazole sodium salt (as the catalyst) which is prepared by refluxing a mixture of imidazole and metal sodium in anhydrous THF for 30 to 60 minutes. The mixture is stirred at room temperature for ten several to several tens of hours to give the desired diacyl compound.

The labelled compounds, i.e. the 1,2-diacyl-3-glycerylphosphorylcholines wherein one or both of the diacy groups are a residue of a fatty acid labelled with an isotope, can be prepared by using an acylating agent wherein the acyl group is a residue of a fatty acid labelled with an isotope (e.g. $^{14}C$ or $^{3}H$) in the same manner as in case of the non-labelled compounds. Alternatively, when monoacyl-3-glycerylphosphorylcholines are used as the starting material, the acyl group thereof may be labelled with an isotope.

The isolation of the desired compound from the reaction mixture obtained above can be carried out as follows:

To the reaction mixture is added chloroform and the mixture is neutralized with 1N HCl-methanol. After adding thereto an appropriate amount of diluted methanol, the mixture is separated into two layers in a separatory funnel. The under layer is taken out and condensed under reduced pressure. The residue is dissolved in ethanol-choloroform-water (7:1:3 by volume) and the resulting solution is passed through a column filled with Amberlite MB-3 type resin, and then the column is washed with ethanol-chloroform-water (7:1:3 by volume). The passed solution and the washing solution are combined and condensed. The resulting condensate is subjected, for instance, to silica gel column chromatography, which is a conventional purification method, to give the desired product in a high yield and in a high purity.

In the present invention, both of the saturated and unsaturated fatty acids can be used under mild conditions, i.e. without through severe conditions for converting them into an acid chloride or acid anhydride as in the conventional methods, and the fatty acids can be converted into 1-acylimidazole under mild conditions (e.g. at room temperature), which can be used for the reaction with GPC or monoacyl derivative thereof or the salt thereof, as it is. Moreover, since the present acylating reaction is carried out in the presence of a specific catalyst, the reaction proceeds under mild condition (e.g. at room temperature) to give the desired compound in a high yield and is a high purity. Accordingly, the present invention is particularly favorable for the introduction of the residue of unstable, highly unsaturated fatty acids, more particularly for the preparation of the mixed acids type lecithins (in the present specification, the mixed acids type lecithins include the compound wherein one of the acyl groups is labelled with an isotope).

Thus, according to the present invention, the desired 1,2-diacyl-3-glycerylphosphorylcholines, particularly the mixed acids type lecithins, more particularly, the labelled lecithins can be prepared in a high yield and in a high purity.

The present invention is illustrated by the following Examples but is not limited thereto.

EXAMPLE 1

In a 100 ml three-necked flask, N,N'-carbonyldiimidazole (1.62 g, 1 × $10^{-2}$ mol) is suspended in dry THF (10 ml), and thereto is added a solution of linoleic acid (2.1 g, 7.5 × $10^3$ mol) in THF (15 ml). The mixture is stirred with a magnetic stirrer under nitrogen gas at room temperature for 28 hours (the moisture is hindered as possible).

To the reaction mixture thus obtained are added a suspension of cadmium chloride salt of GPC (1.1 g, 2.5 × $10^{-3}$ mol) in THF (20 ml) and a solution of imidazole sodium salt [which is prepared by heating with reflux imidazole (1 g) and metal sodium (0.1 g) in THF (10 ml) for 1 hour]in THF (2.5 ml). The mixture is stirred at room temperature for 43 hours. To the reaction mixture is added chloroform (200 ml) and further the mixture is neutralized with 1N HCl-methanol (12 ml). To the mixture are added water (60 ml) and methanol (100 ml). The mixture is separated into two layers in a separatory funnel, and the under layer is taken out and then condensed. The resulting residue is dissolved in ethanol-chloroform-water (7:1:3 by volume, 40 ml) and the solution is passed through a column filled with Amberlite MB-3 type resin (40 ml, which is activated with the same solvent as above) and then the column is washed with the same solvent as above. The passed solution and the washing solution are combined and condensed under reduced pressure. The condensate is dissolved in chloroform-methanol (98:2 by volume) and passed through a column filled with silica gel (60 g, which is treated with the same solvent (chloroform-methanol) as above). The substances adsorbed on the column are eluted with chloroform-methanol (98:2 by volume, 100 ml), chloroform-methanol (6:4 by volume, 1,200 ml) and chloroform-methanol (2:8 by volume, 1,000 ml) to give Fraction I, Fraction II and Fraction III, respectively. The Fraction II is condensed under reduced pressure to give the desired 1,2-dilinoleoyl-L-3-glycerylphosphorylcholine (1.80 g, 90%).

This product is a colorless, sticky compound and shows a single spot in a thin layer chromatography using the following solvent systems (as the developer):

(1) $CHCl_3$—$CH_3OH$—$H_2O$ (65:25:4 by volume) (for phospholipid)
(2) $CHCl_3$—$CH_3OH$—$CH_3COOH$—$H_2O$ (25:15:4: 2 by volume) (for phospholipid)
(3) Petroleum ether-Ethyl ether-$CH_3COOH$ (90:10:1 by volume) (for fatty acid)

which means that the product does not contain any free fatty acid, imidazole or lysolecithin. Besides, the Rf value of this spot is identical to that of the purified lecithin (in yolk). Further, it shows the following optical rotation and elementary analysis.

Optical rotation
$[\alpha]_D^{27} = +7.3°$ ($CHCl_3$:$CH_3OH$ = 1:1, C = 4.4)
$[\alpha]_D^{27} = +7.4°$ ($CHCl_3$:$CH_3OH$ = 1:1, C =4.2)

Elementary analysis for $C_{44}H_{82}O_9NP$: Calcd (%): N,1.68; P,3.89, P/ester, ½Found (%): N,1.75; P, 3.99, 3.99 P/ester, 1/2.20, 1/2.02

From these data, it is proved that the above product is pure.

EXAMPLE 2

In the same manner as described in Example 1, palmitic acid (1.0 g, 3.8 × $10^{-3}$mol) is dissolved in THF (20 ml) and thereto is added N,N'-carbonyl-diimidazole (810 mg, 5 × $10^3$ mol). The mixture is stirred under nitrogen gas at room temperature for about 3 hours. After adding imidazole sodium salt (100 mg), the mixture is stirred additionally for 30 minutes, and thereto is added cadmium chloride salt of GPC (550 mg) and the mixture is again stirred at room temperature for 96 hours. The resulting reaction mixture is treated in the same manner as described in Example 1 to give the desired 1,2-dipalmitoyl-L-3-glycerylphosphorylcholine (873 mg, 93%) as colorless crystals. Melting point: 235 –236° C., $[\alpha]_D^{22} = +8.1°$ [$CHCl_3$ : $CH_3OH$ = 1:1, C = 6.3)

Elementary analysis for $C_{40}H_{82}O_9NP$ (molecular weight: 752): Calcd (%): C,63.89; H,11.00; N,1.86 Found (%): C,64.24; H,11.09; N,1.93

EXAMPLE 3

Into a dried 50 ml two-necked flask provided with a nitrogen-introducing tube and a condenser with a tube filled with calcium chloride are charged an appropriate amount of glass beads and a rotator for a magnetic stirrer and thereto is further introduced nitrogen gas. Into the flask is charged a solution of N,N'-carbonyldiimidazole (407 mg) and palmitic acid (470 mg) in a small amount of THF. The mixture is stirred at room temperature for 2 hours. To the reaction mixture, without isolating the produced 1-palmitoylimidazole, is added GPC (205 mg) and further is added a solution (3 ml) of imidazole sodium salt in THF which is prepared by reacting sodium hydride (130 mg) and imidazole (500 mg) in THF (10 ml) for 30 minutes). The mixture is reacted at room temperature for 65 hours. The resulting reaction mixture is treated in the same manner as described in Example 1 to give the desired 1,2-dipalmitolyl-L-3-glycerylphosphorylcholine (485 mg, 81%). Melting point: 235°–236° C.

This product is a colorless crystalline compound and shows a single spot in a thin layer chromatography.

EXAMPLE 4

Into the same reaction vessel as used in Example 3 is charged a solution of 4-linoleoyl-3-phenyl-1,2,4-oxadiazol-5-one (3.50 g, 1 × $10^{-2}$ mol) in a small amount of THF and thereto is added cadmium chloride salt of GPC (550 mg, 1.25 × $10^{-3}$ mol). To the mixture is further added sodium salt of 3-phenyl-1,2,4-oxadiazol-5-one (100 mg), and the mixture is reacted at room temperature for 48 hours. The resulting reaction mixture is treated in the same manner as described in Example 1 to give the desired 1,2-dilinoleoyl-L-3-glycerylphosphorylcholine (747 mg, 75%).

This product is a colorless, sticky compound and shows a single spot in a thin layer chromatography, and the infrared spectrum thereof is identical with that of reference standard.

EXAMPLE 5

Synthetic pure 1,2-distearoyl-L-3-glycerylphosphorylcholine (50 mg) is dissolved in ethyl ether (1 ml), and thereto are added a solution of phospholipase $A_2$ (0.5 mg) obtained from Crotalus admanteus venom in 0.2 M boric acid-sodium carbonate buffer (pH 7.0, 0.5 ml) and several drops of a 2.5 M calcium chloride aqueous solution (as an activating agent). The mixture is stirred at room temperature for about 1 hour. The reaction mixture is condensed under reduced pressure and thereto is added a small amount of benzene and the mixture is again condensed to remove completely the moisture. The resulting colorless solid material is dissolved in absolute ethanol, and the solution is filtered to remove off the insoluble materials and to the filtrate is added ethyl ether and the solid material is recrystallized at −20° C. The recrystallization is repeated twice. The resulting crystalline product (25 mg, 77%) is 1-stearoyl-L-3-glycerylphosphorylcholine. This product shows a single spot in a thin layer chromatography [developer: $CHCl_3$—$CH_3OH$—$H_2O$ (65:25:4 by volume)], which is identical with that of reference standard. Besides, according to the analysis of monoglyceride obtained by hydrolyzing the product with phospholipase C, the product has a purity of 95.5% as the 1-acyl type compound.

In accordance with the method by Hanahan et al [D. J. Hanahan et al; J. Biol. Chem., Vol. 235, page 1918 (1960)], the 1-stearoyl-L-3-glycerylphospholylcholine (500 mg) obtained above is dissolved in ethanol (10 ml), and to the solution is added a solution of cadmium chloride ($CdCl_2.2.5H_2O$, 700 mg) in water (0.5 ml) and ethanol (8 ml). The mixture is allowed to stand at room temperature for 2 hours. The precipitating crystals are separated by filtration and washed well with ethanol and ethyl ether to give cadmium chloride salt of 1-stearoyl-L-3-glycerylphosphorylcholine (650 mg, 64%).

The cadmium chloride salt (300 mg, 3.6 × $10^{-4}$ mol) thus obtained is suspended in dry THF (10 ml) and thereto are added 1-palmitolylimidazole (660 mg) and imidazole sodium salt (10 mg). The mixture is stirred at room temperature for 16 hours. After adding chloroform (50 ml), the reaction mixture is neutralized with 1N HCl-methanol (3 ml), and thereto are added water (15 ml) and methanol (25 ml). The mixture is separated by a separatory funnel. The under layer is taken out and condensed. The resulting residue is dissolved in ethanol-chloroform-water (7:1:3 by volume, 10 ml) and the solution is passed through a column filled with Amberlite MB-3 type resin (10 ml, which is activated with the same solvent as above) and then the column is washed with the same solvent as above. The passed solution and the washing solution are combined and condensed under reduced pressure. The condensate is dissolved in cholorform-methanol (98:2 by volume) and passed through a column filled with silica gel (30 g, which is treated with the same solvent (chloroform-methanol) as above). The substances adsorbed on the column are eluted with chloroform-methanol (98:2 by volume, 250 ml), chloroform-methanol (6:4, 300 ml) and chloroform-methanol (2:8 by volume, 250 ml) to give Fraction I, Fraction II and Fraction III, respectively. The Fraction II is condensed under reduced pressure to give the desired 1stearoyl-2-palmitoyl-L-3-glycerylphosphorylcholine (260 mg, 80%) as colorless crystals. Melting point: 223°–235° C., $[\alpha]_D^{20} = +6.0° \pm 0.5°$ (CHCl$_3$, C =10.0)

Elementary analysis for C$_{42}$H$_{86}$O$_9$NP (molecular weight: 780.1): Calcd (%): C,64.66; H,11.11; N,1.80. Found (%): C,64.30; H,11.23; N,1.93.

The 1-palmitoylimidazole used in the above Example is prepared as follows:

In a 100 ml three-necked flask, N,N'-carbonyldiimidazole (810 mg, 5 × 10$^{-3}$ mol) is suspended in dry THF (10 ml), and thereto is added a solution of palmitic acid (1.0 g, 3.8 × 10$^{-3}$ mol) in THF (20 ml). The mixture is stirred with a magnetic stirrer under nitrogen gas at room temperature for 3 hours (the moisture is hindered as possible). After the reaction, the reaction mixture is filtered. The filtrate is concentrated under reduced pressure, and the resulting residue is recrystallized from ethyl acetate to give the desired compound (1.0 g). Melting point: 81°–83° C.

EXAMPLE 6

Synthetic pure 1,2-dipalmitoyl-L-3-glycerylphosphorylchlorine (1,234 mg) is dissolved in ethyl ether (70 ml), and thereto are added a solution of phospholipase A$_2$ (4 mg, which is obtained from Naja naja venom) in water (4 ml), 0.2 M Tris buffer (pH 7.2, 2 ml) and 0.1 M calcium chloride aqueous solution (0.5 ml). The mixture is reacted at room temperature for 4 hours. The resulting reaction mixture is condensed under reduced pressure and then treated in the same manner as described in Example 5. The resulting solid material is recrystallized from ethyl ether at −20° C. to give 1-palmitoyl-L-3-glycerylphosphorylcholine (674 mg, 80%). According to the analysis of monoglyceride obtained by hydrolyzing the product with phospholipase C, the product has a purity of 97.9% as the 1-acyl type compound.

The 1-palmitoyl-L-3-glycerylphosphorylcholine (266 mg, 5.17 × 10$^{-4}$ mol) thus obtained is suspended in dry THF (10 ml), and thereto are added 1-linoleoylimidazole (510 mg, 1.55 × 10$^{-3}$ mol) and imidazole sodium salt (10 mg). The mixture is stirred at room temperature for 70 hours. The resulting reaction mixture is treated in the same manner as described in Example 5, and finally is subjected to a silica gel column chromatography to give the desired 1-palmitoyl-2-linoleoyl-L-3-glycerylphosphorylcholine (342.3 mg, 84%) as a colorless, sticky compound. $[\alpha]_D^{20} = +6.5° \pm 0.5°$ (CHCl$_3$: CH$_3$OH = 1:1, C = 5.0)

Elementary analysis for C$_{42}$H$_{82}$O$_9$NP (molecular weight: 776.1): Calcd (%): N,1.80; P,3.99. Found (%): N,2.11; P,3.60.

This product shows a single spot in a thin layer chromatography, which is identical with that of reference standard. Besides, the infrared spectrum of the product is also identical with that of reference standard.

The 1-linoleoylimidazole used in the above Example is prepared from N,N'-carbonyldiimidazole (1,620 mg) and linoleic acid (2,100 mg) in the same manner as described in Example 5.

EXAMPLE 7

In the same manner as described in Example 5 or 6, 1-linoleoyl-L-3-glycerylphosphorylcholine is prepared from pure 1,2-dilinoleoyl-L-3-glycerylphosphorylcholine by using phospholipase A$_2$ obtained from Crotalus admanteus venom or Naja naja venom.

The 1-linoleoyl-L-3-glycerylphosphorylcholine (352.2 mg, 6.54 × 10$^{-4}$ mol), 1-palmitoylimidazole (594.8 mg, 1.96 × 10$^{-3}$ mol) and imidazole sodium salt (10 mg) are added to dry THF (15 ml), and the mixture is reacted at room temperature for 70 hours. The resulting reaction mixture is treated in the same manner as described in Example 5, and finally is subjected to a silica gel column chromatography to give the desired 1-linoleoyl-2-palmitoyl-L-3-glycerylphosphorylcholine (302.6 mg, 58.9%) as a colorless, sticky compound. $[\alpha]_D^{20} = +6.5° \pm 0.5°$ (CHCl$_3$ : CH$_3$OH = 1:1, C =5.0)

Elementary analysis for C$_{42}$H$_{82}$O$_9$NP (molecular weight: 776.1): Calcd (%): N,1.80; P,3.99. Found (%): N,1.78; P,3.80.

This product shows a single spot in a thin layer chromatography, which is identical with that of reference standard. Besides, the infrared spectrum of the product is also identical with that of reference standard.

What is claimed is:

1. A process for preparing a 1,2-diacyl-3-glycerylphosphorylcholine of the formula:

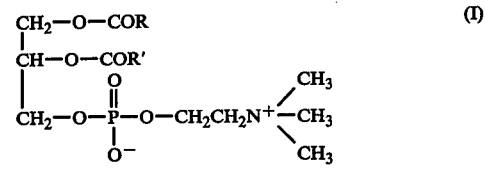

wherein R and R' are the same and are each a residue of a saturated fatty acid having 10 to 22 carbon atoms or an unsaturated fatty acid having 14 to 20 carbon atoms, which comprises acylating glyceryl-phosphorylcholine or a cadmium chloride salt thereof with an acylating agent selected from the group consisting of 1-acylimidazole and 4-acyl-3-phenyl-1,2,4-oxadiazol-5-one in the presence of a catalyst selected from the group consisting of an alkali salt of a nitrogen-containing 5-membered heterocyclic compound and sodium oxide in anhydrous tetrahydrofuran.

2. The process according to claim 1, wherein the acylating agent is a 1-acylimidazole, in which the acyl group is a residue of a saturated fatty acid having 10 to 22 carbon atoms or an unsaturated fatty acid having 14 to 20 carbon atoms.

3. The process according to claim 2, wherein the acyl group of the 1-acylimidazole is a residue of an unsaturated fatty acid selected from the group consisting of myristoleic acid, palmitoleic acid, oleic acid, linoleic acid, linolenic acid and arachidonic acid.

4. The process according to claim 2, wherein the acyl group of the 1-acylimidazole is labelled with an isotope selected from the group consisting of $^{14}C$ and $^3H$.

5. The process according to claim 1, wherein the catalyst is a member selected from the group consisting of imidazole sodium salt, triazole sodium salt and benzimidazole sodium salt.

6. A process for preparing a 1,2-diacyl-3-glycerylphosphorylchlorine of the formula:

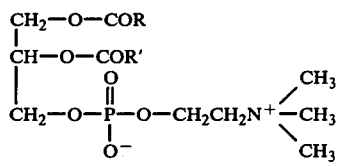

wherein R and R' are different from each other and are each a residue of a saturated fatty acid having 10 to 22 carbon atoms or an unsaturated fatty acid having 14 to 20 carbon atoms, which comprises acylating a 1-monoacyl-3-glycerylphosphorylcholine of the formula:

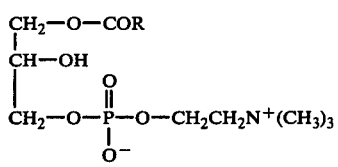

wherein R is a residue of a saturated fatty acid having 10 to 22 carbon atoms or an unsaturated fatty acid having 14 to 20 carbon atoms or a cadmium chloride salt thereof with an acylating agent selected from the group consisting of 1-acylimidazole and 4-acyl-3-phenyl-1,2,4-oxadiozol-5-one wherein the acyl group is a residue of a saturated fatty acid having 10 to 22 carbon atoms or an unsaturated fatty acid having 14 to 20 carbon atoms in the presence of imidazole sodium salt in anhydrous tetrahydrofuran at room temperature.

7. The process according to claim 6, whrein the R group is the formula (III) is a residue of a saturated fatty acid having 10 to 22 carbon atoms.

8. The process according to claim 6, wherein the R group in the formula (III) is a residue of an unsaturated fatty acid having 14 to 20 carbon atoms.

9. The process according to claim 8, wherein the unsaturated fatty acid is a member selected from the group consisting of myristoleic acid, palmitoleic acid, oleic acid, linoleic acid, linolenic acid and arachidonic acid.

10. The process according to claim 6, wherein the acyl group of the acylating agent is a residue of a saturated fatty acid having 10 to 22 carbon atoms.

11. The process according to claim 10, wherein the acyl group is labelled with an isotope selected from the group consisting of $^{14}C$ or $^3H$.

12. The process according to claim 6, wherein the acyl group of the acylating agent is a residue of an unsaturated fatty acid having 14 to 20 carbon atoms.

13. The process according to claim 12, wherein the unsaturated fatty acid is a member selected from the group consisting of myristoleic acid, palmitoleic acid, oleic acid, linoleic acid, linolenic acid and arachiodonic acid.

14. The process according to claim 12, wherein the acyl group of the acylating agent is labelled with an isotope selected from the group consisting of $^{14}C$ and $^3H$.

15. A process for preparing a 1,2-diacyl-3-glycerylphosphorylcholine of the formula:

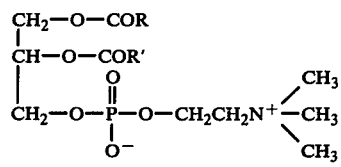

wherein R and R' are different from each other and are each a residue of a saturated fatty acid having 10 to 22 carbon atoms or an unsaturated fatty acid having 14 to 20 carbon atoms, which comprises acylating a 2-monoacyl-3-gylcerylphosphorylchlorine of the formula:

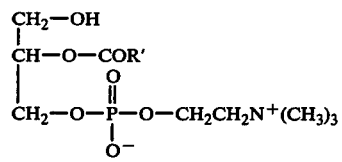

wherein R' is a residue of a saturated fatty acid having 10 to 22 carbon atoms or an unsaturated fatty acid having 14 to 20 carbon atoms or a cadmium chloride salt thereof with an acylating agent selected from the group consisting of 1-acylimidazole and 4-acyl-3-phenyl-1,2,4-oxadiazol-5-one wherein the acyl group is a residue of a saturated fatty acid having 10 to 22 carbon atoms or an unsaturated fatty acid having 14 to 20 carbon atoms in the presence of imidazole sodium salt in anhydrous tetrahydrofuran at room temperature.

16. The process according to claim 15, wherein the R' group in the formula is a residue of a saturated fatty acid having 10 to 22 carbon atoms.

17. The process according to claim 15, wherein the R' group in the formula is a residue of an unsaturated fatty acid having 14 to 20 carbon atoms.

18. The process according to claim 17, wherein the unsaturated fatty acid is a member selected from the group consisting of myristoleic acid, palmitoleic acid, oleic acid, linoleic acid, linolenic acid and arachidonic acid.

19. The process according to claim 15, wherein the acyl group of the acylating agent is a residue of a saturated fatty acid having 10 to 22 carbon atoms.

20. The process according to claim 19, wherein the acyl group is labelled with an isotope selected from the group consisting of $^{14}C$ or $^3H$.

21. The process according to claim 15, wherein the acyl group of the acylating agent is a residue of an unsaturated fatty acid having 14 to 20 carbon atoms.

22. The process according to claim 21, wherein the unsaturated fatty acid is a member selected from the group consisting of myristoleic acid, palmitoleic acid, oleic acid, linoleic acid, linolenic acid and arachidonic acid.

23. The process according to claim 21, wherein the acyl group of the acylating agent is labelled with an isotope selected from the group consisting of $^{14}C$ and $^3H$.

* * * * *

UNITED STATES PATENT AND TRADEMARK OFFICE
CERTIFICATE OF CORRECTION

PATENT NO. : 4,130,571
DATED : December 19, 1978
INVENTOR(S) : Nakajima et al

It is certified that error appears in the above-identified patent and that said Letters Patent are hereby corrected as shown below:

In Column 1, line 29, change "(RCO-13)" to --(RCO-)

Column 5, in the formula (line 5) change "$-CH_2CH_2N+(CH_3)_3$" to -- $-CH_2CH_2N^+(CH_3)_3$ --

Column 6, line 36, change "$7.5 \times 10^3$ mol" to --$7.5 \times 10^{-3}$ mol--

Column 7, line 35, change "$5 \times 10^3$ mol" to --$5 \times 10^{-3}$ mol--

Column 9, line 20, change "223°C" to --233°C--

Signed and Sealed this

First Day of May 1979

[SEAL]

Attest:

RUTH C. MASON
*Attesting Officer*

DONALD W. BANNER
*Commissioner of Patents and Trademarks*